(12) United States Patent
Joseph

(10) Patent No.: US 10,317,319 B2
(45) Date of Patent: Jun. 11, 2019

(54) SAMPLING POINT ASSEMBLY

(71) Applicant: Xtralis Global, Dublin (IE)

(72) Inventor: Steve William Joseph, Portland, OR (US)

(73) Assignee: Xtralis Global, Dublin (IE)

(*) Notice: Subject to any disclaimer, the term of this patent is extended or adjusted under 35 U.S.C. 154(b) by 366 days.

(21) Appl. No.: 15/045,468

(22) Filed: Feb. 17, 2016

(65) Prior Publication Data
US 2016/0238495 A1    Aug. 18, 2016

Related U.S. Application Data

(60) Provisional application No. 62/116,997, filed on Feb. 17, 2015.

(51) Int. Cl.
*G01N 1/26* (2006.01)
*G01N 1/22* (2006.01)
*G01N 15/06* (2006.01)

(52) U.S. Cl.
CPC .............. *G01N 1/2273* (2013.01); *G01N 1/26* (2013.01); *G01N 15/06* (2013.01)

(58) Field of Classification Search
CPC ................. F16B 13/0808; F16B 21/02; G01N 2001/2285; G01N 2001/2291; G01N 1/26
USPC .................. 285/208, 139.1, 140.1, 203, 210; 411/344, 33; 403/85; 73/866.5
See application file for complete search history.

(56) References Cited

U.S. PATENT DOCUMENTS

| 4,974,455 A | * | 12/1990 | McGowan | G01N 1/2258 73/863.12 |
| --- | --- | --- | --- | --- |
| 5,297,432 A | * | 3/1994 | Traina | G05D 11/03 73/23.31 |
| 5,466,015 A | * | 11/1995 | Berenter | F16L 5/00 285/12 |
| 5,586,789 A | * | 12/1996 | Bently | A47L 9/242 285/205 |
| 5,665,924 A | * | 9/1997 | Cole | G01N 1/26 73/863.81 |
| 5,752,724 A | * | 5/1998 | Bormioli | F16L 23/036 285/18 |
| 5,901,985 A | * | 5/1999 | Raatz | F16L 37/1235 267/153 |

(Continued)

FOREIGN PATENT DOCUMENTS

WO    WO 9323735 A1 * 11/1993 ............... G01N 1/26

*Primary Examiner* — Son T Le
*Assistant Examiner* — Alexander A Mercado
(74) *Attorney, Agent, or Firm* — Boyle Fredrickson, S.C.

(57) ABSTRACT

A sampling point assembly for an aspirating particle detection system includes a sampling point body having a bore running from an inlet at a first end of the bore to an outlet at a second end of the bore, the inlet being configured to be maintained in fluid communication with a volume being sampled to receive an air sample therethrough, and the outlet being configured to be coupled to a conduit such that the air sample can pass through the central bore to the conduit. A fastening mechanism includes at least one surface adjacent the inlet and arranged in use to support the sampling point assembly on a first side of a mounting structure, and at least one fastening actuator for holding the surface against the mounting structure from the first side. A cap conceals the fastening mechanism and inlet from view from the first side of the mounting structure.

10 Claims, 11 Drawing Sheets

(56) References Cited

U.S. PATENT DOCUMENTS

| | | | | |
|---|---|---|---|---|
| 6,857,328 B1* | 2/2005 | Spurgeon | ............. | G01N 1/2202 |
| | | | | 73/863.21 |
| 2007/0295112 A1* | 12/2007 | Swank | ................. | G01N 1/2273 |
| | | | | 73/864 |
| 2011/0232335 A1* | 9/2011 | Johnson | ................ | D06F 39/088 |
| | | | | 68/19 |
| 2013/0255357 A1* | 10/2013 | Anderson | ................ | G01N 1/22 |
| | | | | 73/31.01 |
| 2017/0045415 A1* | 2/2017 | Williamson | ........ | G01M 3/2815 |

* cited by examiner

SAMPLING POINT ASSEMBLY

CROSS-REFERENCE TO A RELATED APPLICATION

This application claims priority under 35 USC § 1.119(e) to earlier U.S. Provisional Patent Application Ser. No. 62/116,997, filed Feb. 17, 2015 and entitled Sampling Point Assembly, the contents of which are incorporated by reference in their entirety.

BACKGROUND OF THE INVENTION

1. Field of the Invention

The present invention relates to a sampling point assembly for use in an aspirating particle detection system.

2. Discussion of the Related Art

In aspirating particle detection systems, such as those that use the Vesda® range of smoke detectors manufactured by Xtralis Pty Ltd, a network of sampling pipes is routed over an area to be monitored by the particle detection system. Each sampling pipe includes one or more air sampling points through which air samples are drawn into the system for analysis.

In their simplest form a sampling point may be a hole in the sampling pipe or more commonly are a fitting that couples to the pipe. Such fittings typically take the form of a hollow generally cylindrical body with a frusto-conical tip with a hole at its end, into which air is drawn. Such a fitting can be directly connected to the air sampling pipes, e.g. by being interposed in the pipe or attached to a T-junction directly, or connected to the sampling pipe by a sampling conduit. In use, air is drawn into the air sampling points and into the particle detector by an aspirator. The aspirator typically forms part of the particle detector.

The aspirator delivers sample air drawn from the ambient air in the sample location or volume (e.g. room or cabinet etc.) that is being monitored to the detector at a known flow rate. As will be appreciated the flow rate will vary depending on system parameters, but will typically be in the range of 10 to 150 liters per minute.

In order to ensure correct operation of the system, maintenance of the sample pipe network and sampling points is required. During this maintenance it is necessary to rectify any blockages of sampling holes or sampling pipes. In general this is a manual process undertaken by a technician and can be quite time consuming, and hence costly. During maintenance access to the sampling points or pipes may be required from either within the sample location or from a neighbouring space in which the sampling pipe is located, such as within the ceiling space above the sample location.

During installation it is desirable that the sampling point can be installed in a mounting structure, such as a ceiling, floor or wall panel, or equipment cabinet panel, without removal of the mounting structure or access to a neighbouring space that lies on a second side of the structure, e.g. such as a ceiling space above a room, in which a sample pipe and other services may be located. This makes installation more straightforward for technicians as access to the neighbouring space is not needed.

It is therefore desirable to provide a sampling point assembly that is simple to install and remove and/or that minimises blockage within the sampling point.

It is therefore desirable to provide a sampling point assembly that is simple to install and remove and/or that minimises blockage within the sampling point.

Another perceived issue with existing sampling points is that their visibility from within the sampling location may be considered undesirable in some situations or by some people, e.g. architecturally designed spaces, galleries or the like. Thus, a sampling point with minimal visual impact may be desirable.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

According to a first aspect, the present invention provides a sampling point assembly for an aspirating particle detection system, the sampling point assembly being configured to be mounted to a mounting structure associated with a volume to be sampled, the mounting structure comprising a panel-like portion having a first side and a second side and a space passing through the panel-like portion between the first side and second side that is able to receive the sampling point assembly, and at least the first side of the panel-like portion being exposed to the volume, the sampling point assembly being further configured to be coupled to a conduit to deliver an air sample from the volume being sampled to the conduit, the sampling point assembly including:

a sampling point body having a bore running from an inlet at a first end of the bore to an outlet at a second end of the bore, said inlet being configured to be maintained in fluid communication with the volume being sampled to receive an air sample therethrough, and said outlet being configured to be coupled to the conduit such that the air sample can pass through the bore to the conduit; and fastening mechanism for securing the sampling point body to the mounting structure, said fastening mechanism including at least one mounting surface arranged in use to support the sampling point assembly on the first side of the mounting structure, and at least one fastening actuator for holding the surface against the mounting structure from the first side;

a cap mounted with respect to the sampling point body such that it extends over the fastening mechanism to conceal the fastening mechanism and inlet from view from the first side of the mounting structure.

The cap is preferably removable to provide access to the fastening mechanism. The cap may include a central mounting arrangement, which is inserted into the inlet. The mounting arrangement may have a one or more openings, e.g. slots or holes, to permit passage of air into the inlet. There may be three slots, whereby they are spaced 120 degrees apart creating three resilient prongs. Each prong preferably includes a projection which may be seated in an annular slot in the bore adjacent the inlet. The projections are positioned to space the cap from the inlet, such that an opening or gap is created around the perimeter of the cap to permit the passage of air towards the inlet.

The fastening mechanism preferably includes a flange. The flange may be disc-shaped or any other suitable shape. A first side of the flange preferably comprises a first surface able to be at least partially visible from the first side of the mounting structure, when the sampling point is mounted to it. The second side of the flange can include the mounting surface. Preferably the mounting surface is flat and is arranged to sit against the first side of the mounting structure when the sampling point is mounted to it.

Advantageously, the flange is contoured on the first side. At the periphery of the first surface of the flange is preferably a raised annular lip that surrounds a central recessed area. When the cap is fitted to the sampling point, the cap preferably sits over the central recess, leaving the annular lip of the flange exposed to view from the first side of the mounting structure. The opening around the perimeter of the cap may be a ring created between the lip and the cap. Alternatively, the cap may extend to the edge or past the peripheral edge of the flange and not leave an exposed lip.

The central recess preferably includes a series of projections that operate as standoffs, which assist in maintaining the gap between the cap and remainder of the first surface of the flange.

The annular lip of the flange preferably displays text and/or graphics. The text and/or graphics may be positioned on a surface of the lip that is visible when the cap is fitted, and the sampling point mounted to the mounting structure. The cap may also or alternatively have a surface on its outer side that may be used to display text or graphics, for example a company logo.

The text or graphics may be moulded, e.g. either embossed or impressed, in the lip and/or cap. Alternatively, the text may be provided as a sticker or directly printed on the lip and/or cap. Other mechanisms for permanently displaying text or graphics may be used.

According to a second aspect, the present invention provides a sampling point assembly for an aspirating particle detection system, the sampling point assembly being configured to be mounted to a mounting structure associated with a volume to be sampled, the sampling point assembly being further configured to be coupled to a conduit to deliver an air sample from the volume being sampled to the conduit, the sampling point assembling including:

a sampling point body having a bore running from an inlet at a first end of the bore to an outlet at a second end of the bore, said inlet being configured to be maintained in fluid communication with the volume being sampled to receive an air sample therethrough, and said outlet being configured to be coupled to the conduit such that the air sample can pass through the bore to the conduit; and wherein a restrictor, being an opening of a predetermined size, is provided in the bore between the inlet and the outlet to determine the flow characteristics of sampling point; and wherein the sampling point includes a surface leading into at least the inlet that is inwardly inclined towards the inlet, and said bore includes a surface leading towards the restrictor that is inwardly inclined.

Preferably, the diameter of the restrictor is less than the diameter of the outlet.

The surface leading into the inlet may be part of a flange. The flange may be disc-shaped or any other suitable shape. A first side of the flange preferably comprises a first surface able to be at least partially visible from the first side of the mounting structure, when the sampling point is mounted to it. The second side of the flange can include the mounting surface. Preferably the mounting surface is flat and is arranged to sit against the first side of the mounting structure when the sampling point is mounted to it.

Advantageously, the flange is contoured on the first side. At the periphery of the first surface of the flange is preferably a raised annular lip that surrounds a central recessed area. The surface leading from the annular lip to the central recessed area is preferably inwardly inclined, such that there are a plurality of successive inclined surfaces on the air flow path leading between periphery of the first side and the restrictor.

According to a third aspect, the present invention provides a sampling point assembly for an aspirating particle detection system, the sampling point assembly being configured to be mounted to a mounting structure associated with a volume to be sampled, the sampling point assembly being further configured to be coupled to a conduit to deliver an air sample from the volume being sampled to the conduit, the sampling point assembling including:

a sampling point body having a bore running from an inlet at a first end of the bore to an outlet at a second end of the bore, said inlet being configured to be maintained in fluid communication with the volume being sampled to receive an air sample therethrough, and said outlet being configured to be coupled to the conduit such that the air sample can pass through the bore to the conduit; and wherein the second end of the bore has a stepped diameter, whereby the diameter of the second end of the bore reduces in sections along the bore towards the inlet, such that sampling conduits of different outside diameters may be frictionally gripped by corresponding section of the bore with a corresponding diameter.

Advantageously, two to four sections with different diameters are provided. However, it will be appreciated that more may be incorporated.

Preferably, a restrictor, being an opening of a predetermined size, is provided in the bore between the inlet and the outlet to determine the flow characteristics of sampling point. Preferably, the second end of the bore steps down in diameter size from the outlet to the restrictor.

According to a fourth aspect, the present invention provides a sampling point assembly for an aspirating particle detection system, the sampling point assembly being configured to be mounted to a mounting structure associated with a volume to be sampled, the mounting structure comprising a panel-like portion having a first side and a second side and a space passing through the panel-like portion between the first side and second side that is able to receive the sampling point assembly, and at least the first side of the panel-like portion being exposed to the volume, the sampling point assembly being further configured to be coupled to a conduit to deliver an air sample from the volume being sampled to the conduit, the sampling point assembly including:

a sampling point body having a bore running from an inlet at a first end of the bore to an outlet at a second end of the bore, said inlet being configured to be maintained in fluid communication with the volume being sampled to receive an air sample therethrough, and said outlet being configured to be coupled to the conduit such that the air sample can pass through the bore to the conduit; and fastening mechanism for securing the sampling point body to the mounting structure, said fastening mechanism including at least one mounting surface and arranged in use to support the sampling point assembly on the first side of the mounting structure, and at least one fastening actuator for clamping the mounting surface against the mounting structure from the first side;

wherein the at least one fastening actuator includes at least one threaded screw having a longitudinal axis and at least one clamping arm translatable along the screw, whereby the arm has a first orientation in which the arm sits against the body to enable the insertion of the sampling point body through the space in the panel-like portion from the first side, and a second orientation in which the arm extends outwardly from the body past the edge of the space in the panel-like portion to enable clamping to the panel-like portion; and, wherein said clamping arm is moveable from the first position to the second position by operation of the fastening actuator.

Preferably rotation of the screw initially causes movement of the clamping arm into to the second position, and continued rotation of the screw causes translation of the clamping arm towards the second side of the mounting structure to clamp against it.

Preferably in the second orientation, the clamping arm is translatable along a track that maintains the clamping arm in the second orientation as the arm translates along the screw.

The arms preferably include a generally vertical slot that aligns with a rail on the track, maintaining the second orientation as the arms translate.

The arm may be generally curved, having a radially inner surface and a radially outer surface. The inner surface preferably corresponds to the outer surface of the sampling point body. The outer surface, when in the first position, preferably corresponds to a predetermined minimum mounting space size.

The track preferably includes an upper roof to prevent the arms from being translated along the screw and unscrewed off the end of the screw.

The fastening mechanism preferably includes a flange. The flange may be disc-shaped or any other suitable shape. A first side of the flange preferably comprises a first surface able to be at least partially visible from the first side of the mounting structure, when the sampling point is mounted to it. The second side of the flange can include the mounting surface.

Further aspects of the present invention and further embodiments of the aspects described in the preceding paragraphs will become apparent from the following description, given by way of example and with reference to the accompanying drawings.

BRIEF DESCRIPTION OF THE DRAWINGS

In order that the invention may be more fully understood, one embodiment will now be described by way of example, with reference to the figures in which.

DETAILED DESCRIPTION OF THE EMBODIMENTS

Figure 1:
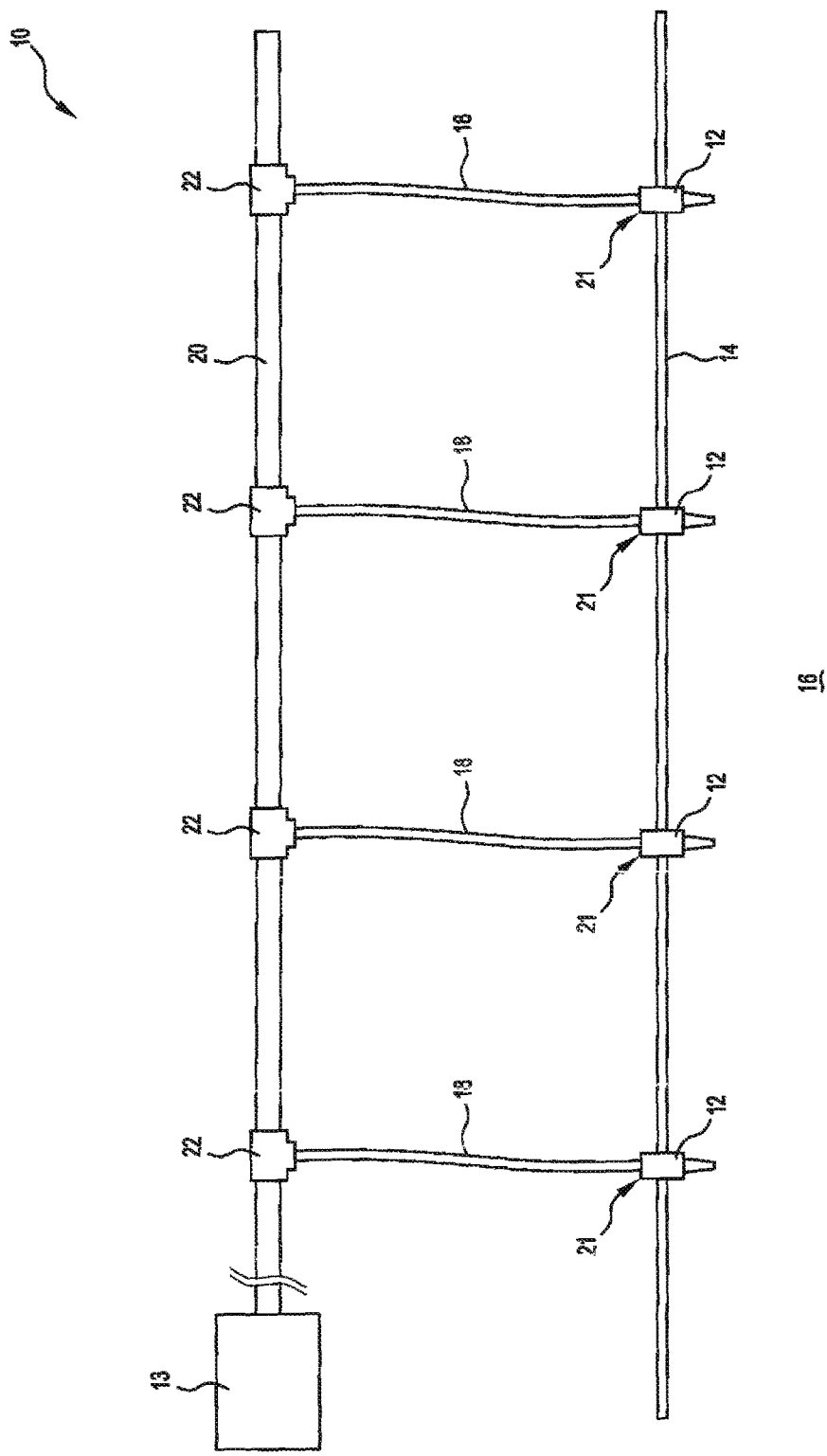
FIG. 1 is a diagram of an exemplary aspirated particle detection system.

The system 10 is arranged to draw an air sample from a volume being monitored, e.g. room 16, and deliver the air sample to a particle detector 13 that may be a smoke detector. Sample air is drawn into the sampling points 12 and travels via sampling conduit 18 to a sampling pipe 20. The sampling conduits 18 are typically connected to the sampling pipe 20 via T-junctions 22. The sample air is drawn into the particle detector 13 for analysis.

There may be a number of such T-junctions 22 along a single length of sampling pipe 20, thereby providing a number of sampling points along a single length of sampling pipe 20. Furthermore, it will be appreciated that a number of sampling pipes 20 can be arranged, e.g. side by side to create a grid, or other geometry of sampling points.

The system is arranged such that the sampling pipe 20 is mounted above a ceiling 14 so only the inlets of the sampling points 12 protrude through apertures 21 in the ceiling 14 to allow sample air to be drawn from within the room 16. In this way the only parts of the particle detection system that is visible from within the room are the sampling points 12.

The present invention provides an improved sampling point assembly 30, which is able to be used as a sampling point 12 in the aspirating particle detector system 10.

In the present description, orientations have been described with respect to the sampling point assembly 30 being fitted within a ceiling to draw an air sample from a room below the ceiling, however, it will be appreciated that sampling point assemblies can be fitted to other mounting structures, such as walls, cabinets, floors, to name but a few, and other orientations. As will be appreciated in the event of mounting in another orientation or surface the description of directions and positions e.g. upper surfaces would be correspondingly changed, e.g. to become side or rear surfaces etc. A person skilled in the art will understand the terminology used.

The exemplary embodiments are also described with reference to a particle detection system in which monitoring of sampled air is performed by an aspirating smoke detector. However, the aspirating particle detection system may be any type of air monitoring system or air sampling device that is be adapted to analyse and/or detect other characteristics or components of the air. For example the air monitoring system or sampling device may be a gas detector or other device capable of detecting the presence and or concentration of one or more target gasses. An example of such an air sampling device is sold by Xtralis Technologies Ltd under the product name Vesda Eco.

Figure 2:
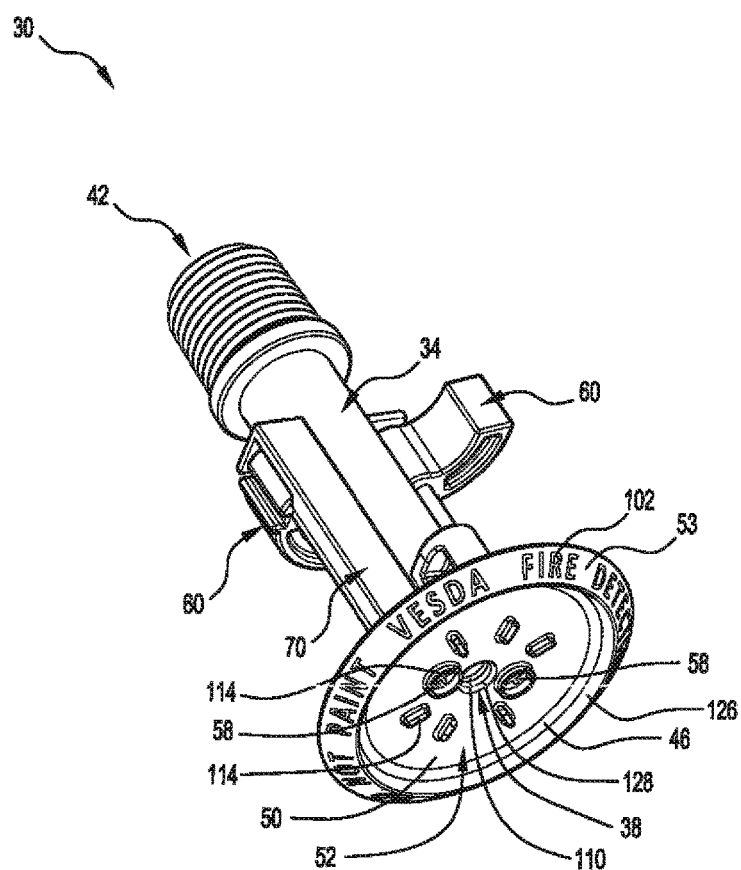
FIG. 2 is an isometric view of a sampling point assembly according to an embodiment of the present invention.

FIG. 2 shows a sampling point assembly 30. The sampling point assembly 30 includes a body 34. The body 34 has a longitudinal bore 36 (best shown in FIG. 3). The bore has an inlet 38 at a first end 40 and an outlet 42 at a second end 44. Sample air is drawn in through the inlet 38, along the bore 36 and into a sampling conduit 18 that may be connected to the outlet. As shown in FIG. 1 the sampling conduit 18 connects to the sampling pipe 20 via a T-junction 22.

The sampling point body 34 (see FIG. 2) terminates at one end in a generally disc-shaped flange 46 that surrounds the inlet 38. The first, upper side 48 of the flange 46 is generally flat so that in use it can abut a surface of a mounting structure substrate to which the sampling point assembly is mounted. The second, lower side 50 of the flange 46 is contoured and cooperates with a cap (shown in FIGS. 8 to 12B) to create a flow path into the inlet 38. At the periphery of the lower side 50 of the flange 46 is a raised annular lip 53. The annular lip 53 surrounds a central recessed area 52 that leads into the inlet 38 at the centre of the flange 46.

Figure 3:
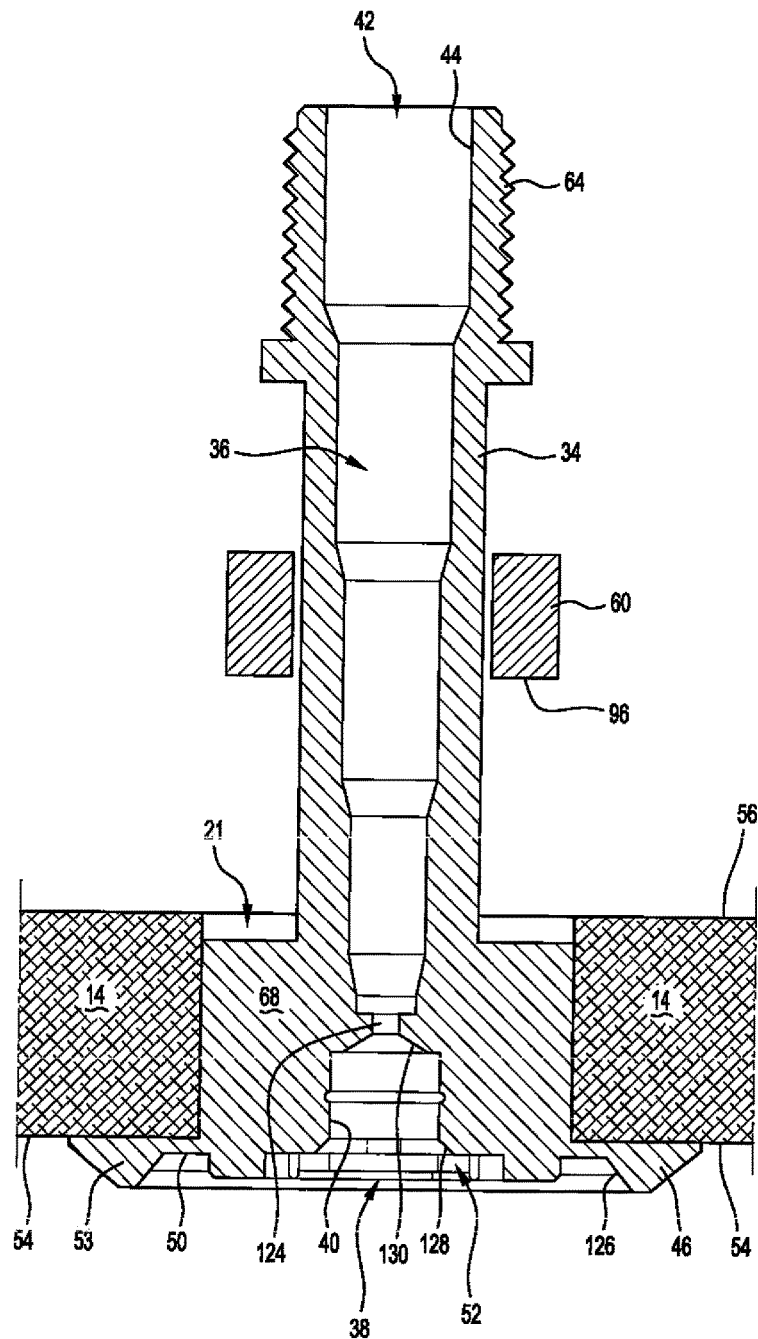
FIG. 3 is a side view of the sampling point assembly of FIG. 2 installed in a mounting structure.

In use, the sampling point assembly 30 is installed through an opening such as an aperture or hole in a mounting structure such that the inlet 34 is positioned on one side of the mounting structure and the outlet is on the other. FIG. 3 illustrates a partial view of the sampling point assembly (excluding its cap and other detail to aid in understanding) that has been installed in a hole 21 in ceiling 14. As can be seen, the sampling point assembly 30 is installed into the ceiling, from below, by insertion through the aperture 21 in the ceiling 14. In this state, the flange 46 sits below the bottom surface 54 of the ceiling 14 such that the flange's flat upper surface 48 bears against the bottom surface 54 of the ceiling 14. The rest of the sampling point body 34 extends upwards through the aperture 21 in the ceiling 14 so that the second end 44 of the sampling point assembly projects above the upper surface 56 of the ceiling 14.

At the second end 44 of the body 34 is an externally threaded portion 64, which will be described further below.

Figure 4:
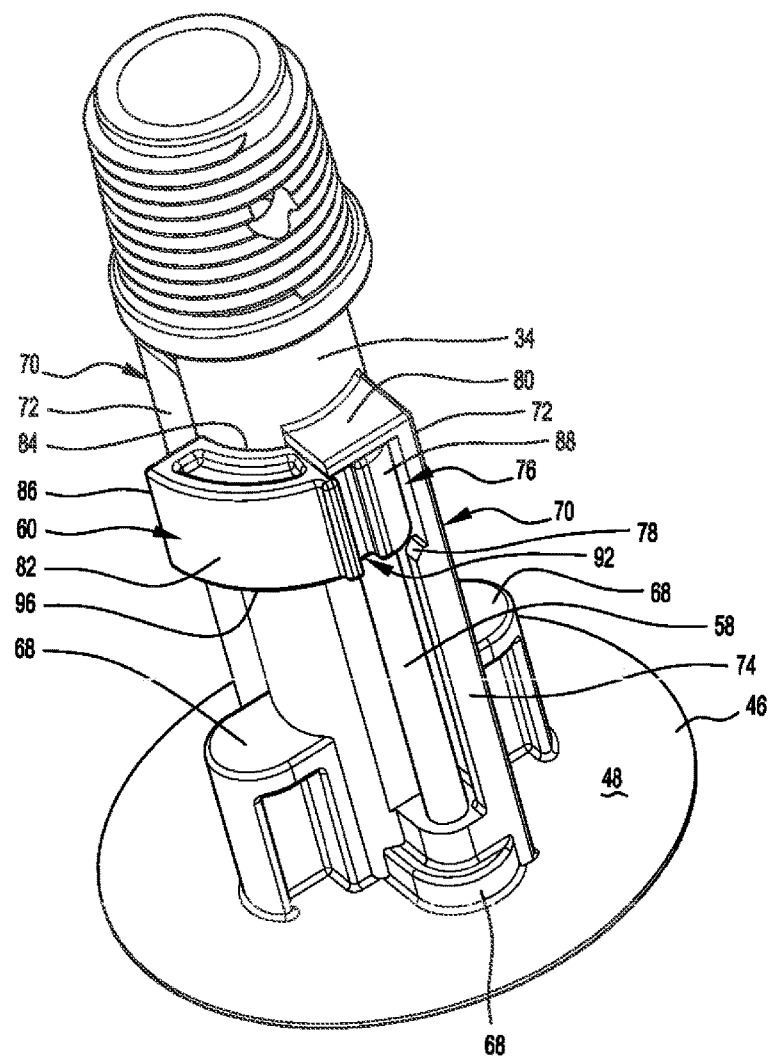
FIG. 4 is a perspective view showing a portion of the fastening mechanism of the sampling point assembly of FIG. 2.

As shown in FIG. 4, at the first end of the body 34, that has the flange 46, there are a series of four shoulders 68 that project from the body 34. The shoulders 68 are arranged around the body 34 at 90 degree intervals. The four shoulders 68 are sized to define points on an outer circumference of the body. The radial distance of these shoulders matches the size of the aperture 21 provided in the ceiling 14 (see FIG. 5). In effect the shoulders 68 define a minimum aperture size into which the sampling point assembly 30 can be mounted. The shoulders 68 provide stability to the body 34 when it is seated in the aperture 21 by preventing lateral movement of the body 34 within the aperture 21.

The sampling point assembly 30 includes a fastening mechanism that is used to attach (preferably removably) the sampling point assembly 30 to a mounting structure. The fastening mechanism in this example generally includes two clamping arms 60 and the first, top surface 48 of the flange 46, and a fastening actuator in the form of two screws 58, each of which correspond to a respective clamping arm 60.

Two screws 58 project through the flange 46 from the lower side 50 of the central recess 52 up through a respective shoulder 68. The head of the screw is accessible from the underside 50 of the flange 46. The screw 58 has a longitudinal axis that generally aligns with the bore 36. The upper ends of the screws 58 are unrestrained from lateral movement. The depth of the shoulders 68 provides an element of lateral support to the base of the screws. A clamping arm 60 is mounted on each screw 58. Each clamping arm 60 has an internally threaded hole that is screwed into the screw 58. An arm 60 is caused to translate along the screw 58 by rotating the screw 58, using a driver tool like a screwdriver, Allen-key or the like.

The clamping arms 60 are shaped as arcs being approximately a ¼ of a circle. The arms have an outer side 82 and an inner side 84, an outer end 86 and an inner end 88. The inner end 88 includes an internally threaded aperture 90 (see FIG. 5) which is threaded onto the screw 58. The arm 60 curves towards its inner side 84 so that its inner side 84 is curved to correspond to the outer curve of the body 34. The outer side 82 of the arm has a corresponding curve.

Also shown in FIG. 4 is a generally vertical track 70. The tracks 70 (one for each clamping arm 60) extend along the side of the body 34. Each track 70 includes a first wall 72 that extends out from the body 34 and a rail portion 74 that extends perpendicularly to the first wall 72. The rail portion 74 does not extend the full length of the first wall 72. Instead a gap 76 is left at its top end. The gap is the same length, or slightly greater than, the height of the arm 60, so that at least part of the arm can be received in the gap 76. The gap 76 creates a ledge 78 at the top of the rail 74. Each track 70 has an upper flange or "roof" 80 that joins back to the body 34. The track 70 aligns with a shoulder 68 so that a screw 58 runs alongside or within the track. The height of the screw 58 is such that the upper end of the screw 58 sits just under the roof 80. The clamping arm 60 is able to sit within the gap 76, between the ledge 78 and the roof 80, with the roof 80 preventing the arm 60 from unscrewing off the end of the screw and falling into the ceiling cavity. Running along the outer side 82 of the arm 60, towards the inner end 88, is a generally vertical slot 92, which corresponds in size to the vertical rail 74. Together the slot 92 and rail 74 cooperate to retain and guide the arm 60 along the track 70 to facilitate reliable clamping of the sampling point assembly 30 to a mounting structure, as will be described in more detail below.

Figure 5:
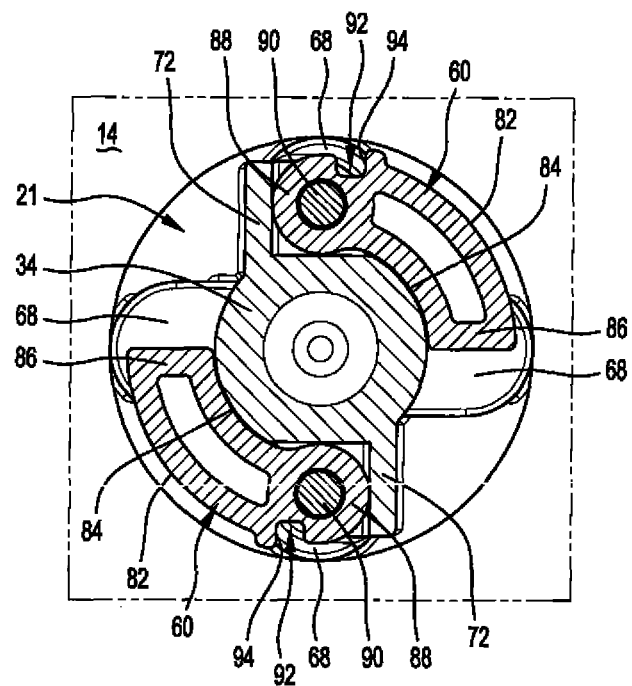
FIG. 5 is a top cross-sectional view of the sampling point assembly being installed.

The arms 60 have a first orientation, as shown in FIGS. 4 and 5. In this first orientation the inner side 84 of the arms 60 sit against the body 34. When both arms 60 are in this first orientation, their outer surface sits at a radius less than, or the same as shoulders 68, so the sampling point body 34 can then be inserted through the aperture 21 from within the room 16.

Figure 6:
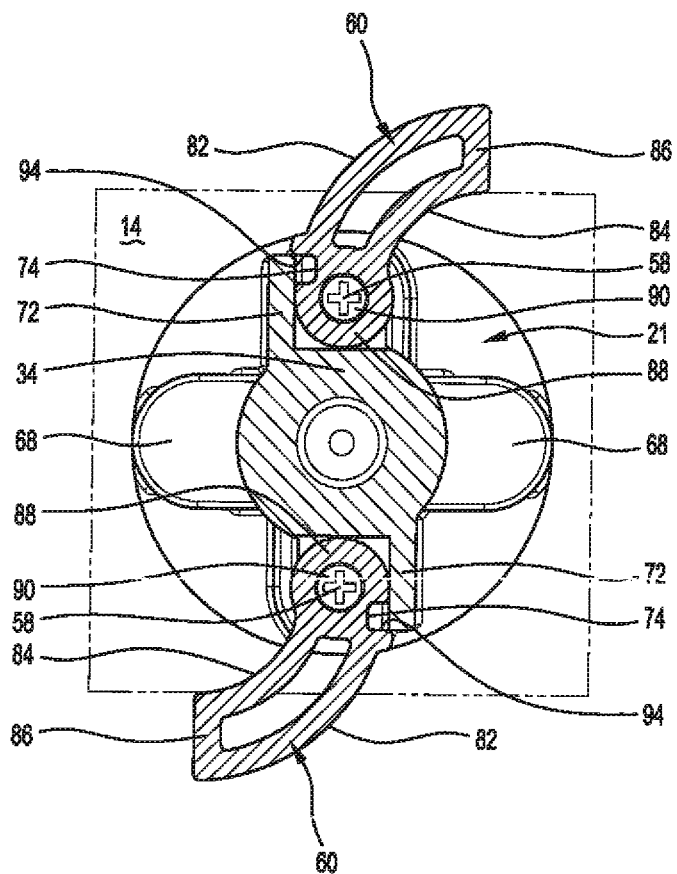
FIG. 6 is a top cross sectional view of the sampling point assembly installed.

The arms 60 can also take a second, extended orientation, as shown in FIG. 6. In the second orientation the arms are rotated outwards, counter-clockwise in this example, so that the wall 94 of the slot 92 abuts against the first wall 72 in the gap 76. This aligns the slot 92 with the rail 74. In this orientation the outer ends 86 of the arms 60 extend radially outward past the shoulder and oppose the first surface 48 of the flange 46. Together the arms and first surface 48 act as a clamp.

Movement between the first and second orientations is effected by the initial rotation of the screws 58. Further rotation of the screw 58 does not cause further rotation of the arms 60 because of the tracks 70. Instead further rotation of the screws 58 translates the arm 60 down the screw 58. Because the rail 74 is retained within the slot 92 the arms 60 are reliably guided down the tracks 70.

Figure 7:
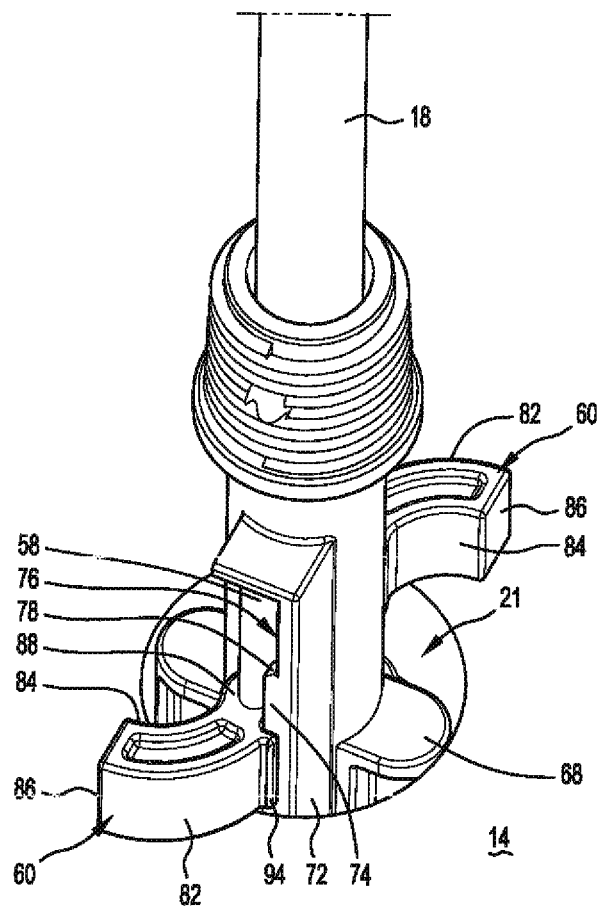
FIG. 7 is a perspective view of the installed sampling point assembly.

The screw 58 can continue to be rotated until the base 96 of the arm 60 abuts against the upper surface 56 of the mounting structure as shown in FIG. 7.

When installing the sampling point assembly 30 into a space, e.g. aperture 21, in a mounting structure, e.g. ceiling 14, the arms 60 are put in the first orientation and the sampling point body 34 and arms are inserted through the aperture from the room 16. The upper surface 48 of the flange 46 abuts the bottom surface 54 of the ceiling 14 and can be held by the installer with one hand. With the other hand the installer can insert a screw driver in the head of each of the screws 58. Rotating the screw 58 approximately 90 degrees moves the arms 60 into a second orientation.

The installer continues to turn the screw 58 until the base 96 of the arm 60 abuts against the upper surface 56 of the ceiling as shown in FIG. 7. By tensioning the screw 58 the ceiling 14 is clamped between the base 96 of the arm 60 and the upper surface 48 of the flange 46 and the sampling point assembly is thereby fastened to the ceiling.

Figure 8:
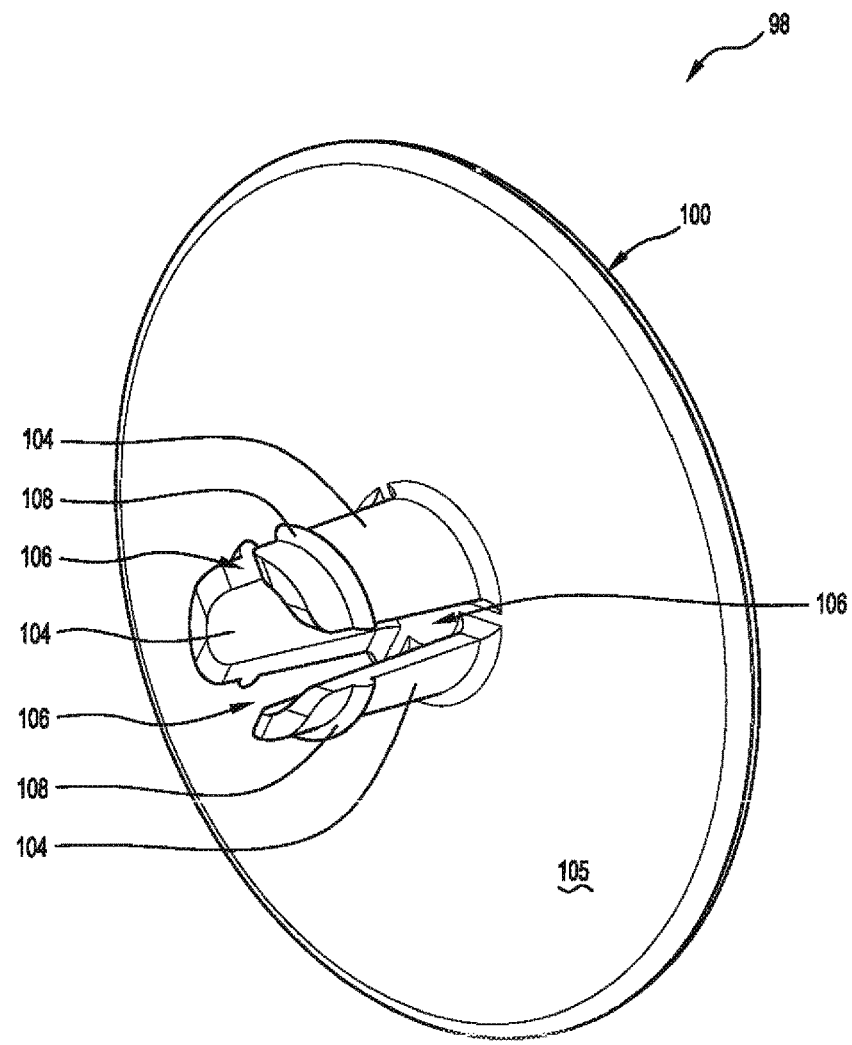
FIG. 8 is a perspective view of the removable cap.

A removable cap 98 is shown in FIG. 8. The cap is used to cover the inlet 38 and if designed in an aesthetically pleasing manner can improve the appearance of the sampling point assembly.

The cap 98 has a lower or outer surface 100 that is generally flat or curved with a large radius. A central mounting arrangement projects from the rear surface 105 in the form of three generally vertical prongs 104. The prongs 104 are separated by slots 106 spaced 120 degrees apart. The prongs 104 are resilient and include a generally horizontal rib 108. The mounting arrangement can be removably inserted into the inlet 38 of the bore 36. As the mounting arrangement is inserted into the inlet 38, the prongs 104 flex inwardly until the ribs 108 lock into a generally horizontal annular groove 110 (see FIGS. 2 and 12A) that runs around the inside of the bore 36 adjacent the inlet 38.

Figure 9:
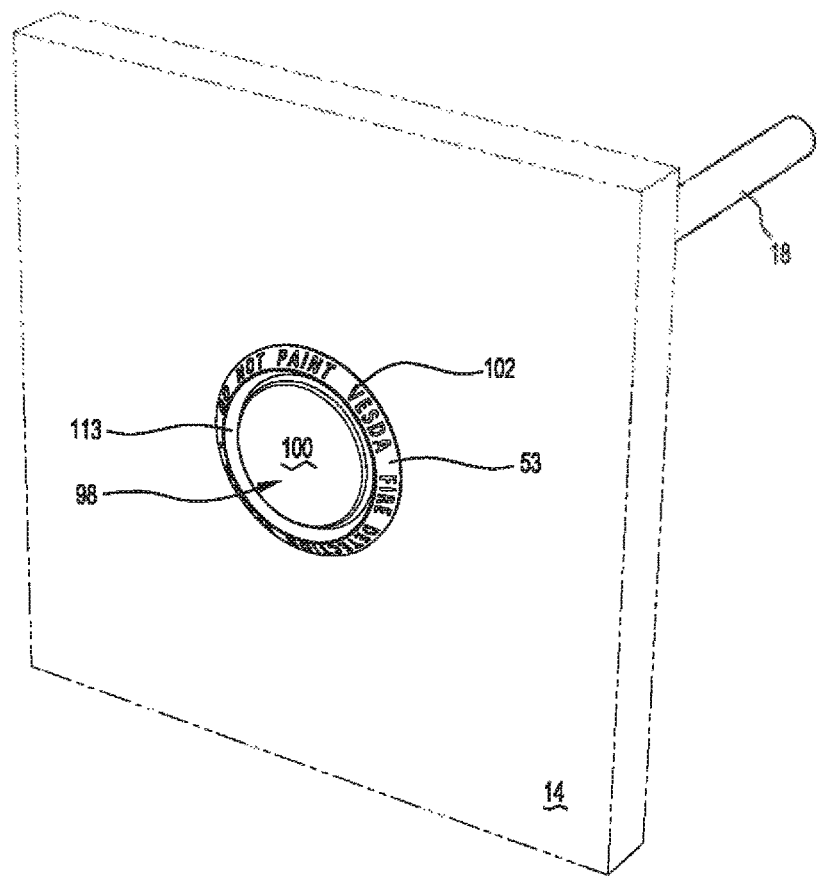
FIG. 9 is an isometric view of a sampling point assembly installed in a ceiling.

The cap 98 has an outer diameter that is less than the inner diameter of the flange annular lip 53. The cap 98 substantially covers the central recess 52 and conceals the bottom of the screws 58 and inlet 38. From within the sample room 16, only the flange lip 53 and the removable cap 98 is visible, as shown in FIG. 9. The depth of the flange 46 and cap 98 form a low profile such that minimal protrusion into the sample room 16 is achieved. The general flat surface of the outer surface 100 of the cap 98 may be smooth and plain to aid in creating an unobtrusive visual impression from within the sample room 16. Alternatively, the lower surface 100 of the cap 98 may be used to display a graphic, such as a company logo or a warning. The graphic may be moulded into the surface, being either embossed or impressed, may be painted or may be provided with a sticker or other method of providing an indicia. The annular lip 53 of the flange 46 also provides a surface onto which text and/or graphics 102 may be provided, as illustrated in the form of impressed writing. In the form illustrated the text carries a warning, that the sampling point is part of a smoke/fire detection system and that it should not be painted. Other desired text, or a warning, such as a statutorily required warning conveniently be displayed on the annular lip.

Figure 10:
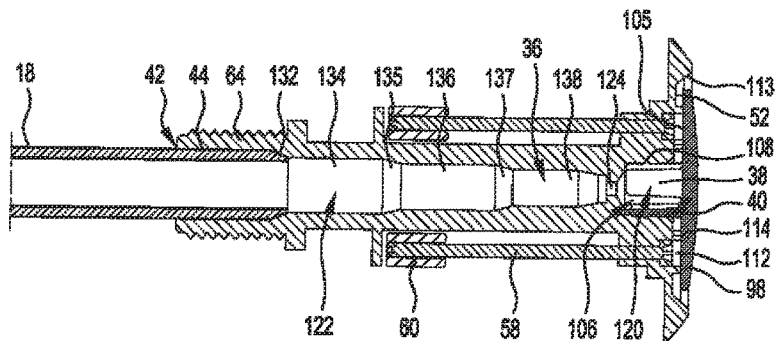
FIG. 10 is cross sectional side view of the sampling point assembly with a conduit of a first diameter.
Figure 11A:
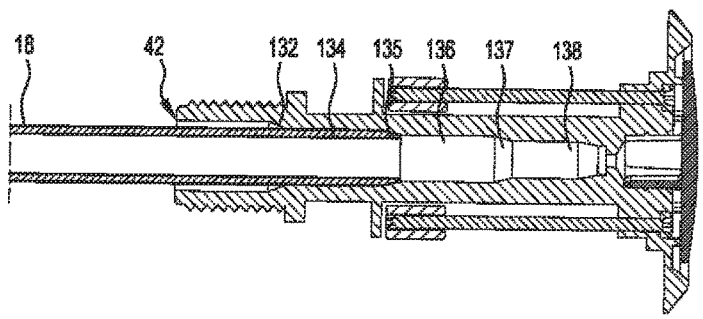
FIG. 11A is a cross sectional side view of the sampling point assembly with a conduit of a second diameter.
Figure 11B:
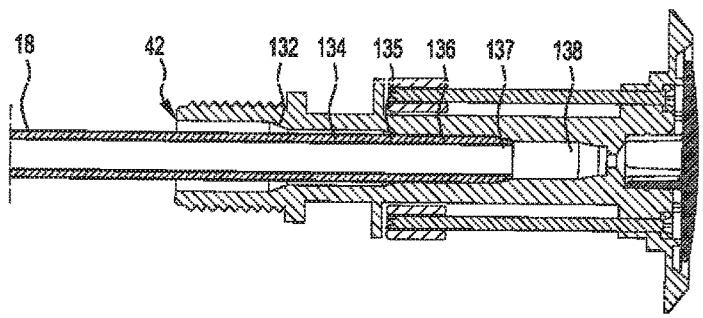
FIG. 11B is a cross sectional side view of the sampling point assembly with a conduit of a third diameter.
Figure 11C:
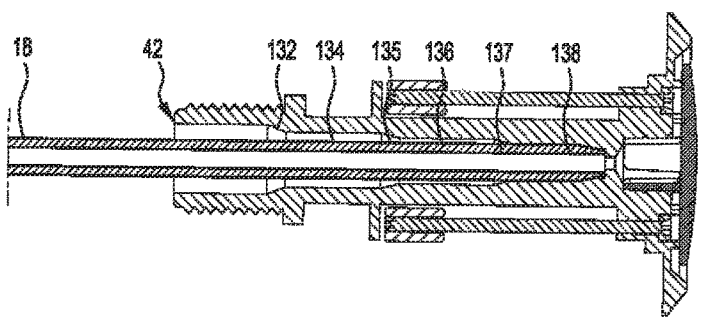
FIG. 11C is a cross sectional side view of the sampling point assembly with a conduit of a fourth diameter.

The location of the ribs 108 on the prongs 104 of the cap 98 and the groove 110 in the inlet are such as to space the rear surface 105 of the cap 98 away from the surface of the central recess 52 (see FIG. 10). This creates a gap 112 underneath the cap 98. Additional standoffs 114 (most clearly seen in FIG. 2) are provided which project from the central recess 52 to maintain the gap 112. An annular opening 113 is created about the edge of the cap (see FIG. 10). Air can pass through the annular opening 113 into the gap 112 of the central recess 52, through the slots 106 in the cap to the inlet 38.

FIG. 10 illustrates how the bore 36 is divided into three portions. The inlet portion 120 is at the first end 40 of the bore. The outlet portion 122 extends inwardly from the second end 44 of the bore 36. The central portion is a restrictor 124, being an opening of a predetermined geometry. The geometry will typically be circular. The restrictor acts as an orifice that determines the flow characteristics through the sampling point assembly. Thus, the diameter of the restrictor 124 is generally smaller than the inlet portion 120. It is also typically smaller than the outlet portion 122 of the bore 36. The restrictor 124 diameter corresponds to a predetermined flow rate for the sample air being drawn from the sample location into the particle detector 13.

The flow path of an air sample into the restrictor 124 progresses radially inwards over the second, contoured side 50 of the flange 46, above the surface 105 of the cap 98 and in doing so passes over transitions between different parts of the surface of the second side 50 (see FIGS. 2 and 3). For example the transition 126 from the lip 53 to the central recess 52; the transition 128 from the central recess 52 to the inlet 38; and the transition 130 from the inlet portion 120 to the restrictor 124. In a preferred form one or more of these transitions are inwardly inclined such that they form an inward tapering of the inlet flow path. These successive inclined, or angled, surfaces 126, 128, 130 reduce clogging of the restrictor orifice. Without seeking to be bound by theory, it is believed that dust and other large contaminant/nuisance particles like dust are more prone to settle on angled surfaces, before they get to the smaller and more easily blocked aperture in the restrictor 124.

FIGS. 10 and 11A to 11C illustrate how the outlet portion 122 of the bore 36 receives a sampling conduit 18. Different applications and installations and even countries or regions may use different diameter conduit for their sampling pipe network.

Therefore a number of different sampling points are typically manufactured with different bore sizes. Thus in order to minimise the need to manufacture a range of different sampling points with different sized bores, and consequently for installers to carry a multitude of different components, at some embodiments the present invention includes an outlet portion 122 of the bore 36 with stepped diameters. The diameter of the bore 36 differs along the length of the outlet portion 122 in sections. As shown successively in FIGS. 10 through 11C, the outlet 42 has a first section with a first diameter, typically of 13 mm (approximately ½ inch) which extends through to a first step 132. The bore 36 then transitions into the second section 134, which has a second diameter, typically of 10 mm (approximately ⅜ inch). The bore 36 then transitions via a second step 135 into third section 136, having a third diameter, typically of 8 mm (approximately 3/16 inch). A third step 137 leads to fourth area 138, having a fourth diameter, typically of 6 mm (approximately ¼ inch). To insert and hold a sampling conduit 18, it can be inserted into the bore until it is gripped by the section of bore with the corresponding diameter and retained by friction.

Figure 12A:
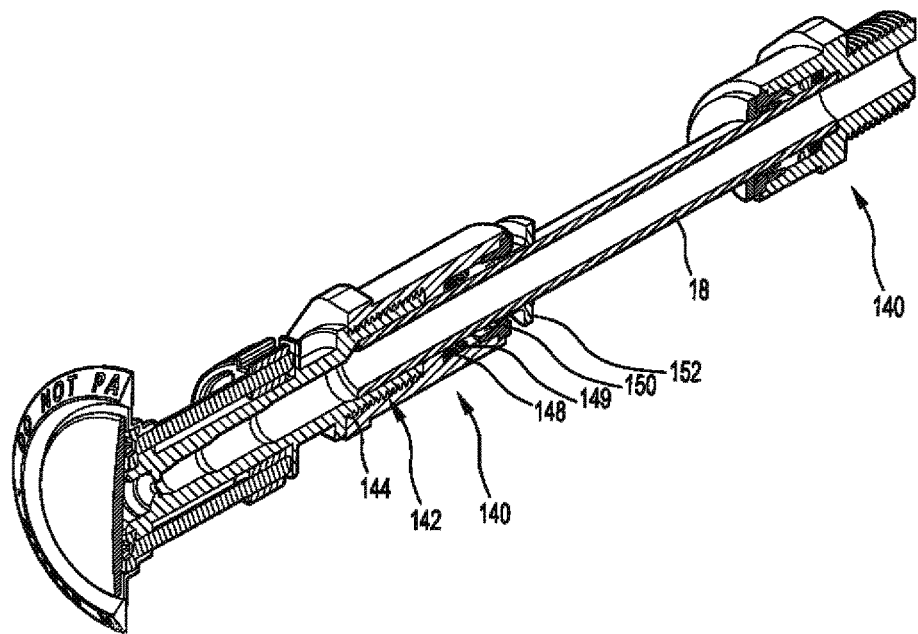
FIG. 12A is a perspective cross sectional view of the sampling point assembly.
Figure 12B:
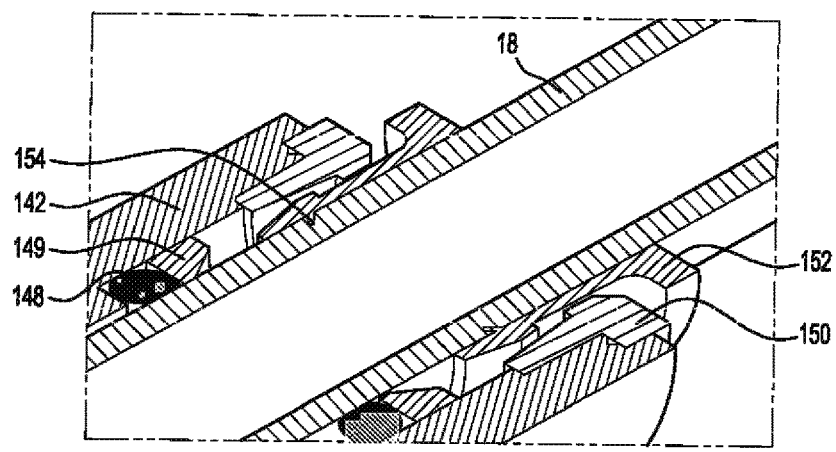
FIG. 12B is an enlarged view of a section of FIG. 12A.

FIG. 10 also shows an external thread 64 at the top of the second end 44 of the bore. The thread 64 generally extends to the first step 132, but may be of any length. As can be seen in FIGS. 12A and 12B, a quick release, push-to-connect fitting 140 is used to retain the sampling conduit 18 in the outlet 42. This fitting 140 is optional, as the bore 36 is sized to create a tight fit between components; however the fitting 140 may advantageously reduce leakage of air between the sampling conduit 18 and the sampling point assembly 30, or provide a connection that is more secure against disconnection.

The fitting 140 includes a body 142, which has a lower section with an internally threaded bore 144. The bore 144 attaches to the thread 64 of the second end 44 of the sampling point body 34. The body 142 includes an O-ring, gasket etc. 148 to seal against the sampling conduit 18 and a lock ring 149 that sits above the O-ring 148. An end ring 150 seals the top of the body 142. A collet 152 sits inside the end ring 150 against the sampling conduit 18 and has inwardly angled projections 154. The projections 154 are best seen in FIG. 12B and engage against the sampling conduit 18 to prevent movement. Alternatively a known, off-the-shelf connector such as a Carstick cartridge could be used.

The upper end of the sampling conduit 18 may also include a push-to-connect fitting 140 for connection to the T-junction 22.

In order to facilitate ease of installation and removal by an installer, slack can be provided in the flexible sampling conduits 18, such that their free end (i.e. the end to be connected to the sampling point assembly) can be pulled through the opening in the support structure into the space being monitored for particles. In this way, during installation, the free end sampling conduit can be connected to the sampling point assembly, as described above, from within the space being monitored. The sampling point assembly can then be mounted to the mounting structure, from within the space being monitored without gaining access to a space on the other side of the mounting structure. Removal of the sampling point, e.g. to enable maintenance, replacement or decommissioning can also be performed from within the room by following the reverse procedure.

As can be seen from the above, embodiments of the present invention may provide a sampling point assembly that has one or more advantageous qualities. For example it may be quick to install and/or remove, and may be installed and/or removed from within the volume being sampled. The low profile of the sampling point and absence of visible fastening means or obvious sampling inlets may also provide a visually appealing, or minimally visually obtrusive appearance from within the volume being sampled.

It will be understood that the invention disclosed and defined in this specification extends to all alternative combinations of two or more of the individual features mentioned or evident from the text or drawings. All of these different combinations constitute various alternative aspects of the invention.

I claim:

1. A sampling point assembly for an aspirating particle detection system, the sampling point assembly being configured to be mounted to a mounting structure associated with a volume being sampled, the mounting structure comprising a panel-like portion having a first side and a second side and a space passing through the panel-like portion between the first side and second side that is able to receive the sampling point assembly, and at least the first side of the panel-like portion being exposed to the volume being sampled, the sampling point assembly being further configured to be coupled to a conduit to deliver an air sample from the volume being sampled to the conduit, the sampling point assembly including:
   a sampling point body having a bore running from an inlet at a first end of the bore to an outlet at a second end of the bore, said inlet being configured to be maintained in fluid communication with the volume being sampled to receive an air sample therethrough, and said outlet being configured to be coupled to the conduit such that the air sample can pass through the bore to the conduit; and
   a fastening mechanism configured to secure the sampling point body to the mounting structure, said fastening mechanism including 1) at least one mounting surface arranged in use to support the sampling point assembly on the first side of the panel-like portion of the mounting structure, and 2) at least one fastening actuator for holding the mounting surface against the mounting structure from the first side of the panel-like portion;
   a cap mounted with respect to the sampling point body such that it extends over the fastening mechanism to conceal the fastening mechanism and the inlet from view from the first side of the panel-like portion of the mounting structure;
   wherein the at least one fastening actuator includes at least one threaded screw having a longitudinal axis and at least one clamping arm translatable along the screw, whereby the clamping arm has a first orientation in which the clamping arm sits against the sampling point body to enable the insertion of the sampling point body through the space in the panel-like portion from the first side, and a second orientation in which the clamping arm extends outwardly from the sampling point body past the edge of the space in the panel-like portion to enable clamping to the panel-like portion; and, wherein the clamping arm is moveable from the first orientation to the second orientation by operation of the fastening actuator;
   wherein rotation of the screw initially causes movement of the clamping arm into to the second orientation, and continued rotation of the screw causes translation of the clamping arm towards the second side of the mounting structure to clamp against it;
   wherein, in the second orientation, the clamping arm is translatable along a track that maintains the clamping arm in the second orientation as the clamping arm translates along the screw;
   wherein the clamping arm includes a generally vertical slot that aligns with a rail on the track, maintaining the second orientation as the clamping arm translates.

2. A sampling point assembly as claimed in claim 1, wherein the cap is removable to provide access to the fastening mechanism.

3. A sampling point assembly as claimed in claim 2, further comprising projections positioned to space the cap from the inlet such that an opening or gap is created around a perimeter of the cap to permit the passage of air towards the inlet.

4. A sampling point assembly according to claim 2, wherein the cap includes a central mounting arrangement which is inserted into the inlet, the mounting arrangement having one or more openings to permit passage of air into the inlet.

5. A sampling point assembly according to claim 1, wherein the fastening mechanism includes a flange, a first side of the flange comprising a first surface capable of being at least partially visible from the first side of the mounting structure, when the sampling point is mounted to it.

6. A sampling point assembly according to claim 5, wherein a second side of the flange includes the mounting surface, the mounting surface being flat and arranged to sit against the first side of the mounting structure when the sampling point is mounted to it.

7. A sampling point assembly according to claim 5, wherein the flange is contoured on a first side thereof and, a raised annular lip is provided at a periphery of a first surface of the flange that surrounds a central recessed area, and wherein, when the cap is fitted to the sampling point, the cap sits over the central recessed area, leaving the annular lip of the flange exposed to view from the first side of the mounting structure.

8. A sampling point assembly according to claim 7, wherein the central recess includes a series of projections which operate as standoffs assisting in maintaining the gap between the cap and remainder of the first surface of the flange.

9. A sampling point assembly according to claim 1, wherein the clamping arm is generally curved, having a radially inner surface and a radially outer surface, the inner surface corresponding to the outer surface of the sampling point body and the outer surface when the clamping arm is in the first orientation thereof, corresponding to a predetermined minimum mounting space size.

10. A sampling point assembly for an aspirating particle detection system, the sampling point assembly being configured to be mounted to a mounting structure associated with a volume being sampled, the mounting structure comprising a panel-like portion having a first side and a second side and a space passing through the panel-like portion between the first side and second side that is able to receive the sampling point assembly, and at least the first side of the panel-like portion being exposed to the volume being sampled, the sampling point assembly being further configured to be coupled to a conduit to deliver an air sample from the volume being sampled to the conduit, the sampling point assembly including:
 a sampling point body having a bore running from an inlet at a first end of the bore to an outlet at a second end of the bore, said inlet being configured to be maintained in fluid communication with the volume being sampled to receive an air sample therethrough, and said outlet being configured to be coupled to the conduit such that the air sample can pass through the bore to the conduit; and
 a fastening mechanism configured to secure the sampling point body to the mounting structure, said fastening mechanism including 1) at least one mounting surface arranged in use to support the sampling point assembly on the first side of the panel-like portion of the mounting structure, and 2) at least one fastening actuator for holding the mounting surface against the mounting structure from the first side of the panel-like portion, the fastening actuator being actuatable from the first side of the panel-like side;
 a cap mounted with respect to the sampling point body such that it extends over the fastening mechanism to conceal the fastening mechanism and the inlet from view from the first side of the panel-like portion of the mounting structure;
 wherein the at least one fastening actuator includes at least one threaded screw having a longitudinal axis and at least one clamping arm translatable along the screw, whereby the clamping arm has a first orientation in which the clamping arm sits against the sampling point body to enable the insertion of the sampling point body through the space in the panel-like portion from the first side, and a second orientation in which the clamping arm extends outwardly from the sampling point body past the edge of the space in the panel-like portion to enable clamping to the panel-like portion on the second side of the panel-like portion; and, wherein the clamping arm is moveable from the first orientation to the second orientation by rotation of the screw from the first side of the panel-like portion;
 wherein rotation of the screw initially causes movement of the clamping arm into the second orientation, and continued rotation of the screw causes translation of the clamping arm towards the second side of the mounting structure to clamp against it;
 wherein, in the second orientation the clamping arm is translatable along a track that maintains the clamping arm in the second orientation as the clamping arm translates along the screw;
 wherein the clamping arm includes generally vertical slot that aligns with a rail on the track, maintaining the second orientation as the clamping arm translates; and
 wherein the track includes an upper roof to prevent the clamping arm from being translated along the screw and unscrewed off the end of the screw.

* * * * *